US00PP24802P3

(12) United States Plant Patent
Korlipara

(10) Patent No.: US PP24,802 P3
(45) Date of Patent: Aug. 19, 2014

(54) *ECHINACEA* PLANT NAMED 'SUNBIRD'

(50) Latin Name: ***Echinacea* hybrid**
Varietal Denomination: Sunbird

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 171 days.

(21) Appl. No.: 13/573,965

(22) Filed: Oct. 16, 2012

(65) Prior Publication Data

US 2014/0109274 P1 Apr. 17, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Sunbird' characterized by large yellow orange ray florets, numerous ray florets which cup down like a "shuttle cock", a medium habit with good branching, strong stems on an upright habit, and excellent vigor.

1 Drawing Sheet

Botanical denomination: *Echinacea* hybrid.
Variety designation: 'Sunbird'.

BACKGROUND OF THE INVENTION

The present invention relates to a new and distinct cultivar of *Echinacea* and given the cultivar name 'Sunbird'. *Echinacea* is in the family Asteraceae. The new cultivar is part of a planned breeding program for a series with compact habits and "shuttle cock" inflorescences. The exact parents of this selection are unknown, unnamed, proprietary interspecific hybrids of *Echinacea paradoxa*×*Echinacea purpurea*.

Compared to *Echinacea* 'Now Cheesier' (U.S. Plant Pat. No. 23,059), the most similar plant on the market, the new variety has darker yellow orange ray florets that which reflex back like a 'shuttlecock' rather than spreading out on a horizontal plane.

This new *Echinacea* cultivar is distinguished by:

1. large yellow orange ray florets,
2. numerous ray florets which reflex back like a "shuttle cock",
3. a medium habit with good branching,
4. strong stems on an upright habit, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the inflorescences of *Echinacea* 'Sunbird' on a two-year-old plant growing in the trial field in full sun in late July in Canby, Oreg.

DETAILED PLANT DESCRIPTION

The following is a detailed description of the new *Echinacea* cultivar based on observations of a three-year-old specimen growing in the trial field in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The *Royal Horticultural Society Colour Chart, 5th* edition.

Plant:

*Type.*—Herbaceous perennial.
*Hardiness.*—USDA Zones 4 to 9.
*Size.*—Grows to about 52 cm wide and 70 cm tall to top of inflorescences.
*Form.*—Basal clump, with about 40 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 5 inflorescences per stem.
*Size.*—To 67 cm tall to a terminal inflorescence and 10 mm wide at base.
*Internode length.*—1.5 cm to 4 cm.
*Surface texture.*—Strigose.
*Color.*—Yellow Green 146B.

Leaf (basal):

*Type.*—Simple.
*Shape.*—Lanceolate.
*Arrangement.*—Basal.

*Blade size.*—Grows to 12 cm long and 3.5 cm wide.
*Margins.*—Coarsely serrate, slightly undulate.
*Apex.*—Acuminate.
*Base.*—Attenuate.
*Surface texture.*—Strigose on both sides.
*Venation.*—Pinnate, with 3 main veins, veins Yellow Green 146C on top and bottom.
*Color.*—Topside Yellow Green 147A bottom side Yellow Green 147B.
*Petiole description.*—Grows to 10 cm long and 3 mm wide, strigose, Yellow Green 147A on leafy sides and Yellow Green 146C in middle.

Leaf (stem):
*Type.*—Simple.
*Shape.*—Lanceolate.
*Arrangement.*—Alternate.
*Blade size.*—Grows to 12 cm long and 3.5 cm wide.
*Margins.*—Entire to coarsely serrate, undulate.
*Apex.*—Acuminate.
*Base.*—Attenuate.
*Surface texture.*—Strigose on both sides.
*Venation.*—Pinnate, with 3 main veins from the base, veins Yellow Green 146C on top and bottom.
*Color.*—Topside Yellow Green 147A, bottom side Yellow Green 147B.
*Petiole description.*—On lowermost leaves only, clasping, grows to 8 cm long and 5 mm wide above the clasp, glabrous, Yellow Green 147C.

Inflorescence:
*Type.*—Composite on terminal stalked heads.
*Number of flowering stems from the ground.*—About 40.
*Flowering stem.*—Grows to 67 cm tall from the base of the plant to the terminal inflorescence and can grow to 13 cm long from the top stem leaf to the base of an inflorescence; branched with 1 to 5 inflorescences per stem; diameter growing to 10 mm wide near the inflorescence; strigose; Yellow Green 146B.
*Size.*—Grows to 10 cm wide and 6 cm deep as disc enlarges.
*Form.*—Ray florets held reflexed and curling back, mature disc is conic.
*Immature inflorescence.*—Grows to 4 cm wide and 2.7 cm deep, ray florets held upright (about 25 degrees from vertical) and rolled up so only the back color shows, Yellow 18A, disc color Yellow Green 144A.
*Ray florets.*—Without pistil or stamen, to 40 in number in two layers, grow to 50 mm long and 7 mm wide, oblanceolate with the tip two to three-toothed (each acute), entire margins, base attenuate, glabrous on both sides; topside Yellow Orange 25A maturing to Yellow Orange 23A, bottom side Yellow Orange 16A with edges Yellow Orange 23A.
*Disc.*—Flat becoming conic, becoming 35 mm deep and 43 mm wide with maturity, Yellow Green 146C in the background and Yellow Orange 26B in the foreground.
*Disc florets.*—About 400 in number, each with 1 pistil and 4 stamen, grow to 11 mm long and 1.5 mm wide, each with one persistent, very stiff linear bract (14 mm long with the top 4 mm colored Yellow Orange 26B on top ¼, then Yellow Green 144A in middle, then White 155A on bottom half); corollas 5.5 mm long and 1.5 mm wide, tubular, 5 lobed, glabrous, Yellow Green 149D except lobes where Yellow Green 146C; pistil 11 mm long, ovary 3.5 mm long, White NN155D, style 5 mm long Yellow Green 145D, 2-branched stigma spreading, Yellow Green 145A; stamen 5.5 mm long, filaments 2 mm long and Yellow Green 145D, anthers 3.5 mm long and Greyed Green 197A, pollen Yellow Orange 16A.
*Phyllaries.*—In 4 leafy series, area grows to 35 mm wide and 7 mm deep, lobes lanceolate in shape, reflexed, grow to 15 mm long and 3 mm wide, Yellow Green 147B, margins strigose, tip acute, strigose on both sides.
*Receptacle.*—Grows to 13 mm wide and 22 mm deep, White 155B.
*Bloom period.*—July through October in Canby, Oreg.
*Fragrance.*—Excellent, floral.
*Lastingness.*—Each inflorescence lasts about two weeks in Canby, Oreg.

Seeds: 3 mm long and 2.5 mm wide, oval, Brown 200C.
*Fertility.*—Good.

Disease and pests: No pests or diseases have been observed on plants grown under commercial conditions in Canby, Oreg. No resistances are known.

I claim:

1. A new and distinct *Echinacea* plant as herein illustrated and described.

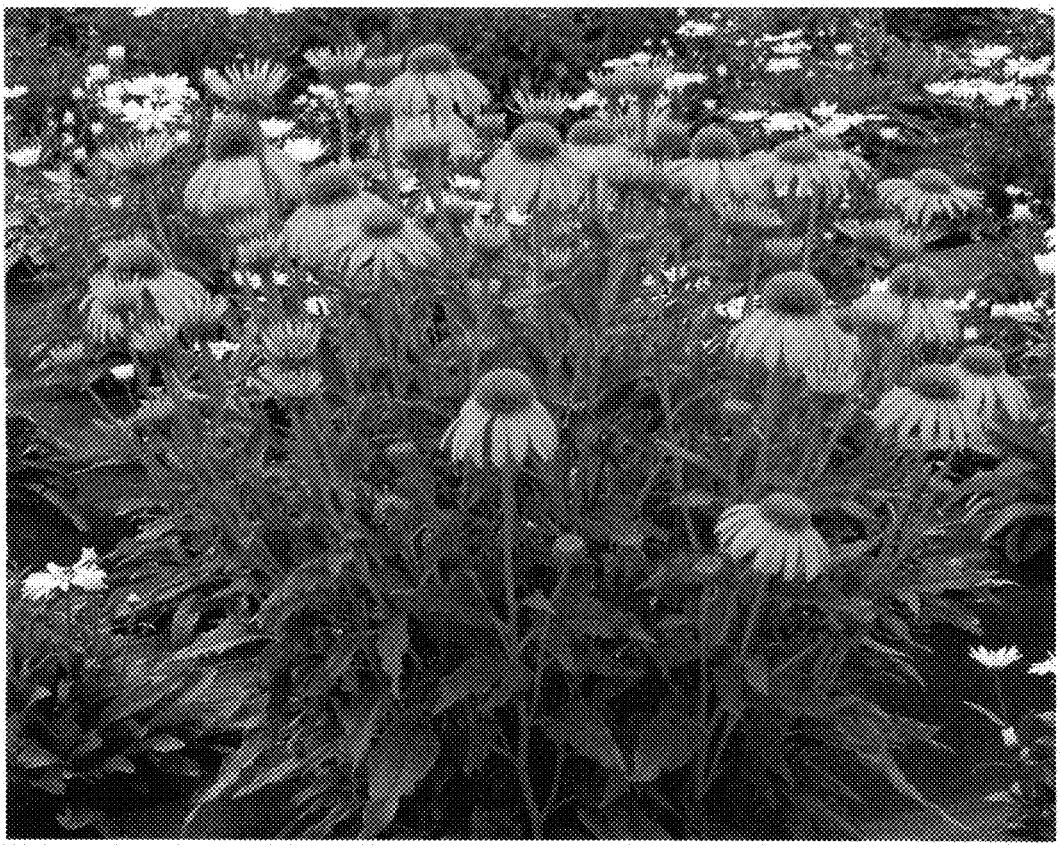

* * * * *